United States Patent
Smith

(10) Patent No.: US 11,951,281 B2
(45) Date of Patent: Apr. 9, 2024

(54) FLUID CONDUIT INSERTION DEVICES

(71) Applicant: MEDTRONIC MINIMED, INC., Northridge, CA (US)

(72) Inventor: Roger E. Smith, Ivins, UT (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 151 days.

(21) Appl. No.: 17/515,721

(22) Filed: Nov. 1, 2021

(65) Prior Publication Data

US 2022/0143307 A1     May 12, 2022

Related U.S. Application Data

(60) Provisional application No. 63/112,573, filed on Nov. 11, 2020.

(51) Int. Cl.
*A61M 5/158* (2006.01)

(52) U.S. Cl.
CPC ..... *A61M 5/158* (2013.01); *A61M 2005/1585* (2013.01)

(58) Field of Classification Search
CPC .......... A61M 5/158; A61M 2005/1585; A61M 2005/14252; A61M 2005/1583; A61M 2205/0272; A61M 2205/8281; A61M 5/14248
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |

(Continued)

FOREIGN PATENT DOCUMENTS

| | | |
|---|---|---|
| WO | 2015164645 A1 | 10/2015 |
| WO | 2018165499 A1 | 9/2018 |
| WO | 2022103869 A1 | 5/2022 |

OTHER PUBLICATIONS

International Search Report dated Mar. 1, 2022 and Written Opinion completed Feb. 21, 2022 corresponding to counterpart Int'l Patent Application PCT/US2021/058828.

*Primary Examiner* — Theodore J Stigell

(74) *Attorney, Agent, or Firm* — Fortem IP LLP

(57) ABSTRACT

Disclosed herein are techniques related to insertion of a fluid conduit (e.g., tubing connected to a fluid reservoir or a cannula sharing a pre-assembled fluid pathway with such tubing). In some embodiments, an insertion mechanism may include one or more springs (e.g., a torsion spring or a compression spring). The one or more springs may cause a trocar or a trocar slider to pierce tissue and insert the fluid conduit. The one or more springs may further cause the trocar or the trocar slider to be removed from the tissue.

20 Claims, 13 Drawing Sheets

(56) References Cited

U.S. PATENT DOCUMENTS

| | | |
|---|---|---|
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Nunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Stoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,672,328 B2 | 6/2017 | Saint et al. |
| 10,130,758 B2 | 11/2018 | Dilanni et al. |
| 10,835,727 B2 | 11/2020 | Montalvo et al. |
| 2007/0123819 A1 | 5/2007 | Mernoe et al. |
| 2008/0051718 A1 | 2/2008 | Kavazov et al. |
| 2010/0160861 A1 | 6/2010 | Causey, III et al. |
| 2010/0217105 A1 | 8/2010 | Yodfat et al. |
| 2015/0238705 A1 | 8/2015 | Gravesen et al. |
| 2019/0015585 A1 | 1/2019 | Smith |
| 2019/0117885 A1 | 4/2019 | Cole et al. |
| 2019/0365987 A1* | 12/2019 | Gibson ............ A61M 5/14248 |
| 2019/0365993 A1 | 12/2019 | Staub et al. |
| 2020/0001005 A1 | 1/2020 | Politis et al. |
| 2020/0108201 A1 | 4/2020 | Ben-David et al. |
| 2020/0327973 A1 | 10/2020 | Pryor et al. |
| 2022/0143302 A1 | 5/2022 | Yavorsky |
| 2022/0143306 A1 | 5/2022 | Yavorsky |

* cited by examiner

FLUID CONDUIT INSERTION DEVICES

CROSS-REFERENCE TO RELATED APPLICATIONS

The present application claims the benefit of and priority to U.S. Provisional Patent Application Ser. No. 63/112,573, filed on Nov. 11, 2020, the entire content of which being hereby incorporated by reference.

TECHNICAL FIELD

This disclosure relates generally to medical insertion devices and, more particularly, to fluid conduit insertion devices.

BACKGROUND

A person may use insulin therapy to manage type I or type II diabetes. Insulin therapy may include use of insulin infusion systems for delivering or dispensing insulin. An insulin infusion system may include an infusion device which typically includes a small motor and drive train components configured to deliver insulin from a reservoir into the body of a person, e.g., via a percutaneous needle or a cannula placed in the subcutaneous tissue. Insulin infusion systems may facilitate management of diabetes for some persons.

SUMMARY

This disclosure relates generally to techniques for inserting medical devices into patients More particularly, this disclosure relates to techniques for inserting fluid conduits (e.g., tubing directly connected to fluid reservoirs or cannulas indirectly connected to fluid reservoirs).

In accordance with aspects of the disclosure, a torsional insertion mechanism includes a torsion spring configured to rotate a crank based on a difference between a first spring state and a second spring state and an insertion assembly coupled to the crank and configured to move from a first position to a second position in response to rotation of the crank. The insertion assembly includes a conduit carrier and a trocar slider configured to pierce tissue. The trocar slider is slidably disposed along the conduit carrier and configured to separate from the conduit carrier upon piercing tissue.

In an aspect of the disclosure, the conduit carrier may include a flexible tube having a distal portion configured for insertion into tissue in response to rotational motion of the crank.

In another aspect of the disclosure, the trocar slider may be configured to pierce tissue in response to rotational motion of the crank.

In yet another aspect of the disclosure, the trocar slider may include a tab configured for moving the conduit carrier into the second position.

In yet a further aspect of the disclosure, the torsional insertion mechanism may further include a housing configured to retain a distal portion of the torsion spring. The torsion spring may include a proximal portion configured to engage with the crank and a slot of the trocar slider.

In an aspect of the disclosure, the torsional insertion mechanism may further include a trigger mechanism configured to selectively enable rotation of the crank.

In another aspect of the disclosure, the insertion assembly may further include a fluid flow path that passes through the flexible tube in the conduit carrier. The fluid flow path may be configured for fluid communication between the distal portion of the flexible tube and a medicament reservoir.

In yet another aspect of the disclosure, the trocar slider and the conduit carrier may be configured to move together from the first position to the second position.

In a further aspect of the disclosure, the trocar slider may be configured to return to the first position from the second position while the conduit carrier remains in the second position.

In accordance with aspects of the disclosure, an infusion pump system includes a torsional insertion mechanism. The torsional insertion mechanism includes a torsion spring configured to rotate a crank, based on a difference between a first spring state and a second spring state and an insertion assembly coupled to the crank and configured to move from a first position to a second position in response to rotation of the crank. The insertion assembly includes a conduit carrier and a trocar slider configured to pierce tissue. The trocar slider is slidably disposed along the conduit carrier and configured to separate from the conduit carrier upon piercing tissue.

In yet another aspect of the disclosure, the conduit carrier may include a flexible tube having a distal portion configured for insertion into tissue in response to rotational motion of the crank.

In a further aspect of the disclosure, the trocar slider may be configured to pierce tissue in response to rotational motion of the crank.

In yet a further aspect of the disclosure, the trocar slider may include a tab configured for moving the conduit carrier into the second position.

In an aspect of the disclosure, the torsional insertion mechanism may further include a housing configured to retain a distal portion of the torsion spring. The torsion spring may include a proximal portion configured to engage with the crank and a slot of the trocar slider.

In another aspect of the disclosure, the torsional insertion mechanism may further include a trigger mechanism configured to selectively enable rotation of the crank.

In an aspect of the disclosure, the trocar slider and the conduit carrier may be configured to move together from the first position to the second position.

In yet another aspect of the disclosure, the trocar slider may be configured to return to the first position from the second position while the conduit carrier remains in the second position.

According to a further aspect of the disclosure, a method for operating a torsional insertion mechanism of an insulin infusion system includes rotating a crank based on a difference between a first spring state and a second spring state of a torsion spring, moving a trocar slider and a conduit carrier from a first position to a second position in response to rotation of the crank, and returning the trocar slider to the first position while leaving the conduit carrier in the second position in response to continued rotation of the crank.

In an aspect of the disclosure, the method may further include moving the trocar slider and the conduit carrier from the first position to the second position includes piercing tissue with at least the trocar slider.

In yet another aspect of the disclosure, returning the trocar slider to the first position while leaving the conduit carrier in the second position may include disengaging the crank from the conduit carrier via an open-ended slot of the conduit carrier.

According to a further aspect of the disclosure, a torsional insertion mechanism, includes a torsion spring configured to rotate a crank based on a difference between a first spring state and a second spring state and an insertion assembly coupled to the crank and configured to move from a first position to a second position in response to rotation of the crank. The insertion assembly includes a cannula carrier and a trocar slider configured to pierce tissue. The trocar slider is slidably disposed along the cannula carrier and configured to separate from the cannula carrier upon piercing tissue.

In an aspect of the disclosure, the cannula carrier may include a cannula configured for insertion into tissue in response to rotational motion of the crank.

In another aspect of the disclosure, the trocar slider includes a trocar slidably disposed inside of the cannula. The trocar is configured to pierce tissue in response to rotational motion of the crank.

In an aspect of the disclosure, the trocar slider includes a tab configured for moving the cannula carrier into the second position.

In yet another aspect of the disclosure, the torsional insertion mechanism may further include a housing configured to retain a distal portion of the torsion spring. The torsion spring includes a proximal portion configured to engage with the crank and a slot of the trocar slider.

In an aspect of the disclosure, The torsional insertion mechanism may further include a trigger mechanism configured to selectively enable rotation of the crank.

In another aspect of the disclosure, the trigger mechanism may be configured to engage a recess in the crank to prevent rotation of the crank and to disengage the recess in the crank to enable rotation of the crank.

In yet another aspect of the disclosure, the insertion assembly may further include a fluid flow path that passes through the cannula in the cannula carrier. The fluid flow path is configured for fluid communication between the cannula and a medicament reservoir.

In an aspect of the disclosure, the trocar slider and the cannula carrier may be configured to move together from the first position to the second position.

In another aspect of the disclosure, the trocar slider may be configured to return to the first position while the cannula carrier remains in the second position.

According to a further aspect of the disclosure, an infusion pump system includes a torsional insertion mechanism. The torsional insertion mechanism includes a torsion spring configured to rotate a crank based on a difference between a first spring state and a second spring state and an insertion assembly coupled to the crank and configured to move from a first position to a second position in response to rotation of the crank. The insertion assembly includes a cannula carrier and a trocar slider configured to pierce tissue. The trocar slider is slidably disposed along the cannula carrier and configured to separate from the cannula carrier upon piercing tissue.

In an aspect of the disclosure, the cannula carrier may include a cannula configured for insertion into tissue in response to rotational motion of the crank.

In another aspect of the disclosure, the trocar slider may include a trocar slidably disposed inside of the cannula. The trocar may be configured to pierce tissue in response to rotational motion of the crank.

In a further aspect of the disclosure, the trocar slider may include a tab configured for moving the cannula carrier into the second position.

In yet a further aspect of the disclosure, the torsional insertion mechanism may further include a housing configured to retain a distal portion of the torsion spring. The torsion spring may include a proximal portion configured to engage with the crank and a slot of the trocar slider.

In an aspect of the disclosure, the torsional insertion mechanism may further include a trigger mechanism configured to selectively enable rotation of the crank.

In another aspect of the disclosure, the trocar slider and the cannula carrier may be configured to move together from the first position to the second position. The trocar slider may be configured to return to the first position while the cannula carrier remains in the second position.

According to a further aspect of the disclosure, a method for operating a torsional insertion mechanism of an insulin infusion system includes rotating a crank based on a difference between a first spring state and a second spring state of a torsion spring, moving a trocar slider and a cannula carrier from a first position to a second position in response to rotation of the crank, and returning the trocar slider to the first position while leaving the cannula carrier in the second position in response to continued rotation of the crank.

In an aspect of the disclosure, moving the trocar slider and the cannula carrier from the first position to the second trocar position includes piercing tissue with the trocar slider.

In another aspect of the disclosure, returning the trocar slider to the first position while leaving the cannula carrier in the second position may include disengaging the crank from the cannula carrier via an open-ended slot of the cannula carrier.

According to a further aspect of the disclosure, an insertion mechanism includes a first compression spring configured to exert a linear force based on a difference between a compressed state and an uncompressed state, an insertion assembly configured to move from a first position to a second position in response to the linear force exerted by the first compression spring. The insertion assembly includes a conduit carrier and a trocar configured to pierce tissue. The conduit carrier includes a first opening through which extends a cannula and a second opening through which extends tubing connected to a fluid reservoir. The trocar being slidably disposed within the cannula.

In an aspect of the disclosure, the conduit carrier and the trocar may be configured to move together from the first position to the second position.

In another aspect of the disclosure, the trocar may be configured to return to the first position while the conduit carrier remains in the second position.

In yet another aspect of the disclosure, the insertion mechanism according may further include a second compression spring configured to return the trocar to the first position.

In a further aspect of the disclosure, the insertion mechanism according may further include a second compression spring coupled to the trocar.

In yet a further aspect of the disclosure, the trocar may be a solid needle integrated with a second compression spring configured to return the trocar to the first position.

In an aspect of the disclosure, the insertion mechanism according may further include a second compression spring configured to move the trocar outside of the cannula.

In another aspect of the disclosure, the conduit carrier may further include a third opening in which a trocar seal is disposed.

In an aspect of the disclosure, the trocar may be slidably disposed within the trocar seal.

In another aspect of the disclosure, a distal end of the trocar may move to a location within the trocar seal when the trocar returns to the first position while the conduit carrier remains in the second position.

According to a further aspect of the disclosure, an infusion pump system include an insertion mechanism. The insertion mechanism may include a first compression spring configured to exert a linear force based on a difference between a compressed state and an uncompressed state and an insertion assembly configured to move from a first position to a second position in response to the linear force exerted by the first compression spring. The insertion assembly includes a conduit carrier and a trocar configured to pierce tissue. The conduit carrier includes a first opening through which extends a cannula and a second opening through which extends tubing connected to a fluid reservoir. The trocar being slidably disposed within the cannula.

In an aspect of the disclosure, the trocar is configured to return to the first position while the conduit carrier remains in the second position.

In another aspect of the disclosure, the infusion pump system may further include a second compression spring configured to return the trocar to the first position.

In yet another aspect of the disclosure, the trocar is a solid needle integrated with a second compression spring configured to return the trocar to the first position.

In an aspect of the disclosure, the infusion pump system may further include a second compression spring configured to move the trocar outside the cannula.

In a further aspect of the disclosure, the conduit carrier further includes a third opening in which a trocar seal is disposed.

In another aspect of the disclosure, a distal end of the trocar moves to a location within the trocar seal when the trocar returns to the first position while the conduit carrier remains in the second position.

According to a further aspect of the disclosure, method for operating an insertion mechanism of an insulin infusion system includes moving a trocar and a conduit carrier from a first position to a second position in response to a force exerted by a first compression spring. The conduit carrier includes a first opening through which extends a cannula and a second opening through which extends tubing connected to a fluid reservoir. The trocar blocks a connection between the cannula and the tubing. The method further includes returning the trocar to the first position while leaving the conduit carrier in the second position in response to a force exerted by a second compression spring, thereby permitting the connection between the cannula and the tubing.

In an aspect of the disclosure, moving the trocar from the first position to the second position may cause the trocar to pierce tissue and insert the cannula in the tissue.

In another aspect of the disclosure, the conduit carrier may further include a third opening in which a trocar seal is disposed. Returning the trocar to the first position may include moving a distal end of the trocar to a location within the trocar seal.

BRIEF DESCRIPTION OF THE DRAWINGS

The above and other aspects and features of the disclosure will become more apparent in view of the following detailed description when taken in conjunction with the accompanying drawings wherein like reference numerals identify similar or identical elements.

DETAILED DESCRIPTION

This disclosure relates generally to techniques for inserting medical devices into patients. More particularly, this disclosure relates to techniques for inserting fluid conduits (e.g., tubing directly connected to fluid reservoirs or cannulas indirectly connected to fluid reservoirs).

As used herein, "exemplary" does not necessarily mean "preferred" and may simply refer to an example unless the context clearly indicates otherwise.

Figure 1:
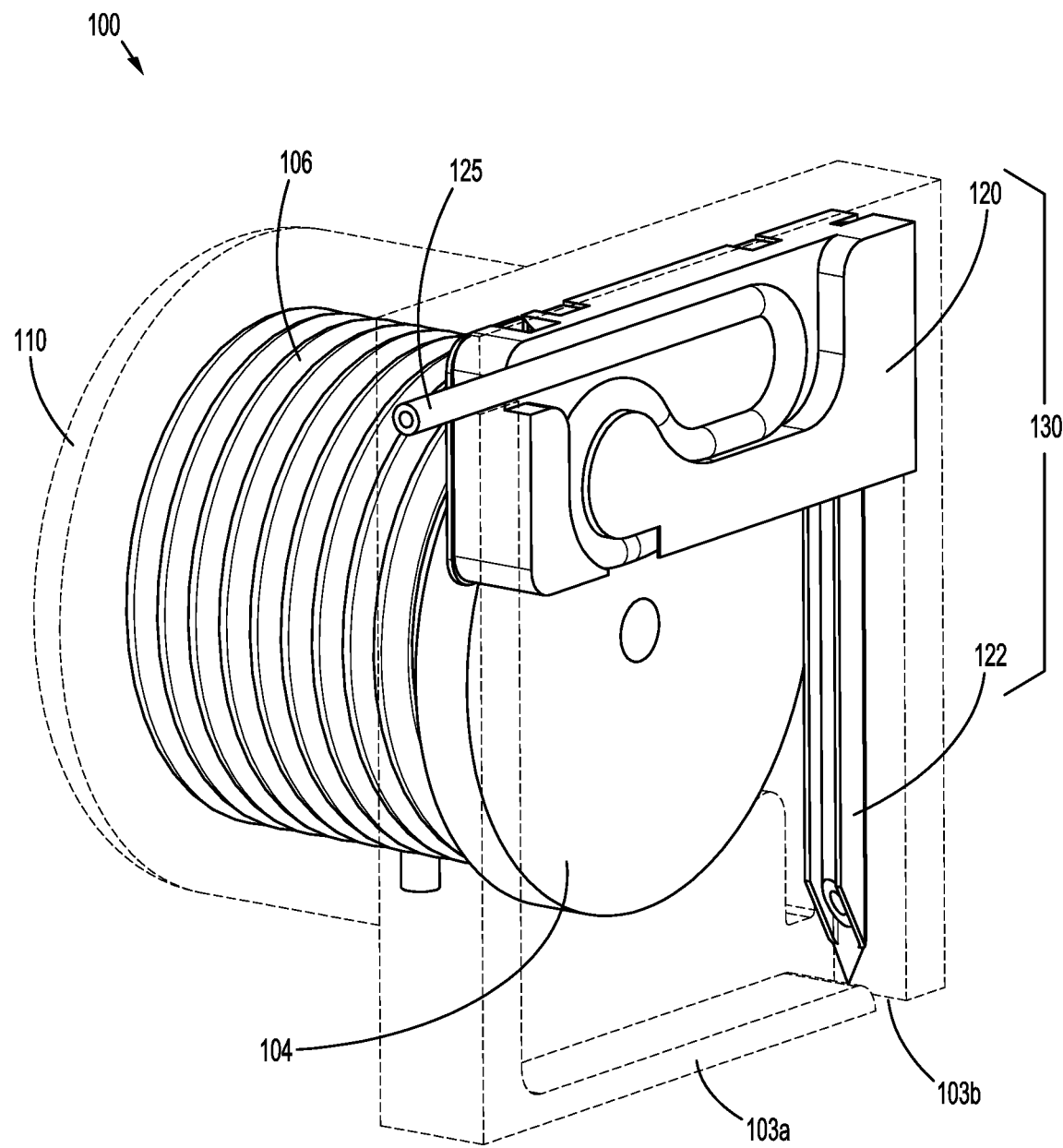
FIG. 1 is an illustration of an exemplary torsional insertion mechanism having a torsion spring in an unfired state, in accordance with aspects of the disclosure.
Figure 2:
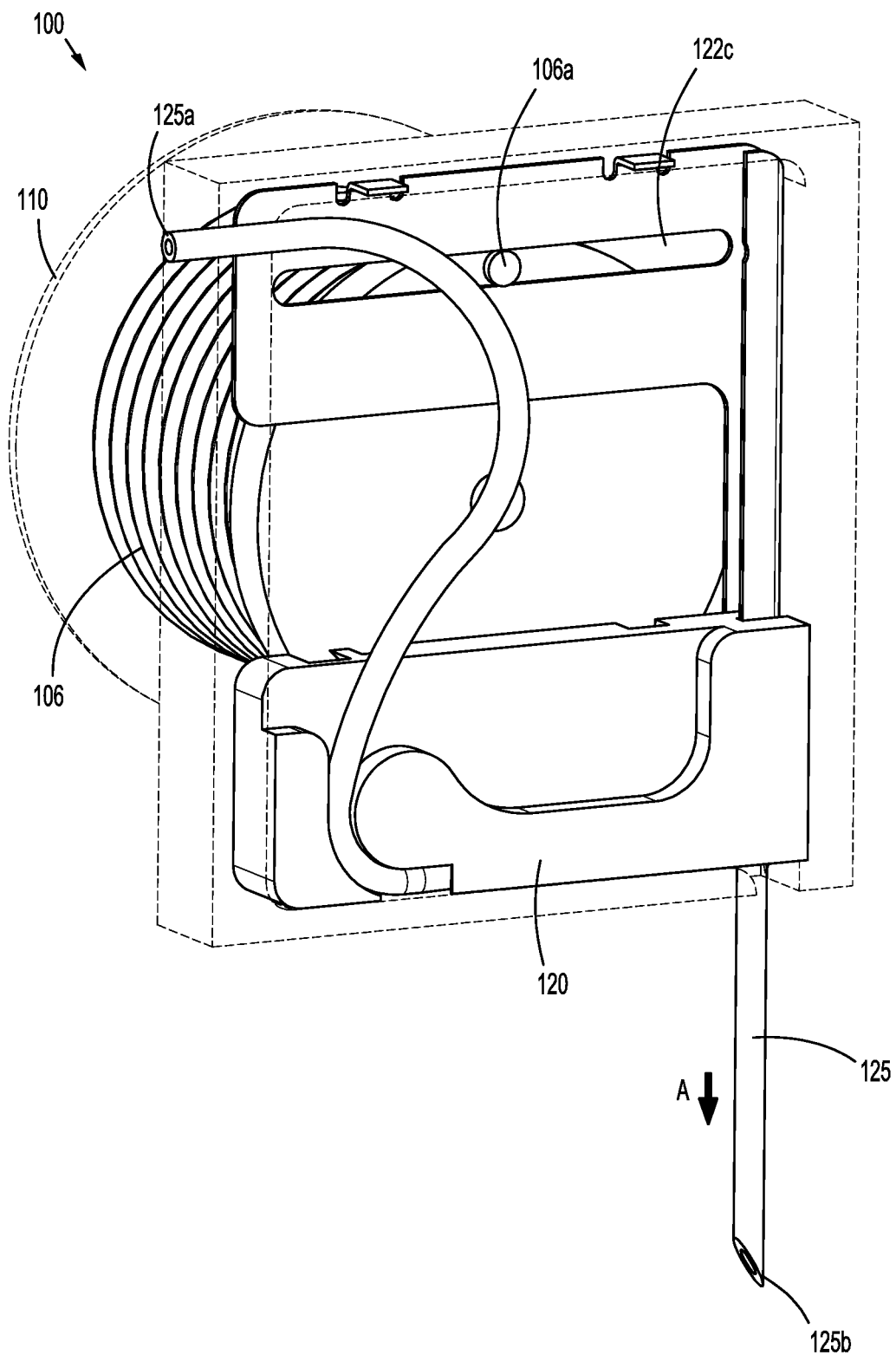
FIG. 2 is an illustration of the torsional insertion mechanism of FIG. 1 having the torsion spring in a fired state, in accordance with aspects of the disclosure.

Referring to FIG. 1, an exemplary torsional insertion mechanism 100 is shown. The torsional insertion mechanism 100 may be a component of an infusion pump system (e.g., 1700 of FIG. 17). The torsional insertion mechanism 100 generally includes a housing 110, a torsion spring 106, a crank 104, and an insertion assembly 130. As will be described in greater detail below, the insertion assembly 130 includes a trocar slider 122 and a conduit carrier 120 configured to carry tubing 125 (e.g., a flexible tube connected to a fluid reservoir). FIG. 1 shows the torsional insertion mechanism 100 in an unfired position. FIG. 2 shows the torsional insertion mechanism 100 in a fired position.

Figure 3:
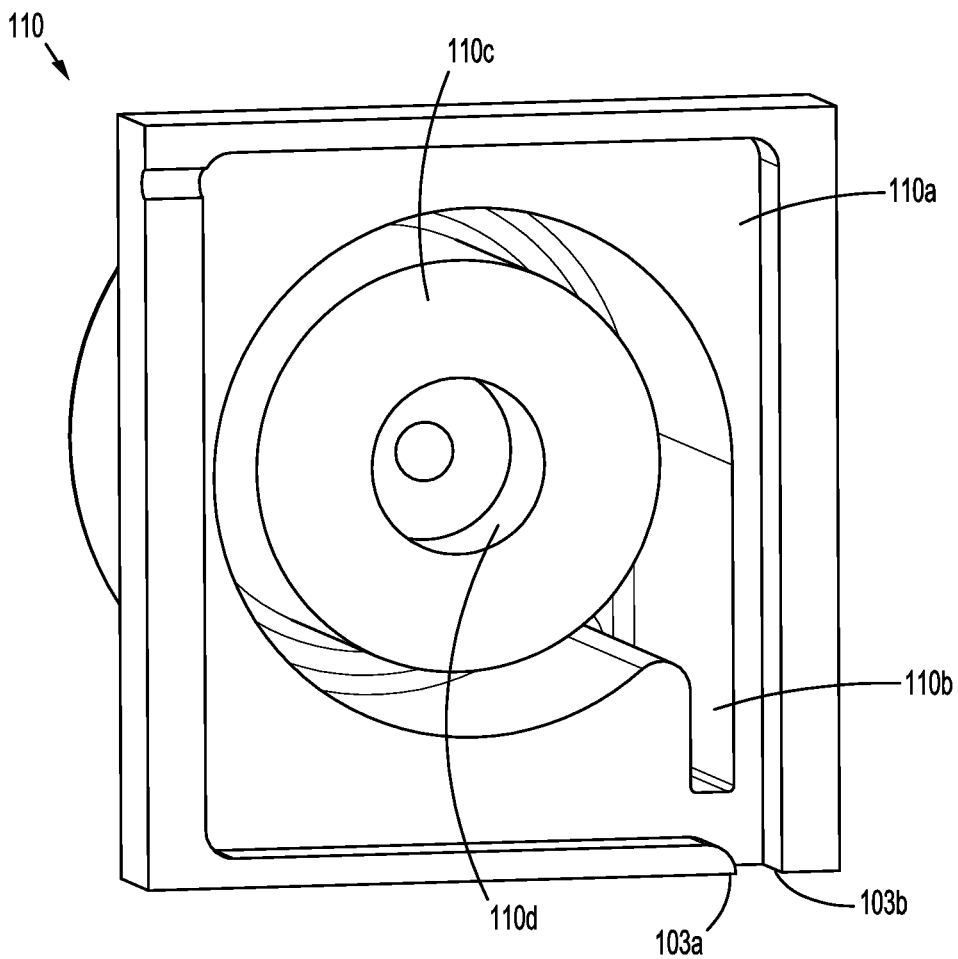
FIG. 3 is a perspective view of a housing of the torsional insertion mechanism of FIG. 1, in accordance with aspects of the disclosure.

Referring to FIG. 3, the housing 110 is configured to house the components of the torsional insertion mechanism 100. The housing 110 generally includes a recess 110b configured to retain a distal portion 106b of the torsion spring 106 (FIG. 4), a boss 110c configured to accommodate and/or guide the torsion spring 106, a bore 110d, and a guide defined by housing fingers 103a and 103b configured to guide the insertion assembly 130 (FIG. 1) by enabling vertical travel of the insertion assembly 130 when the torsion spring 106 fires (FIG. 2).

Figure 4:
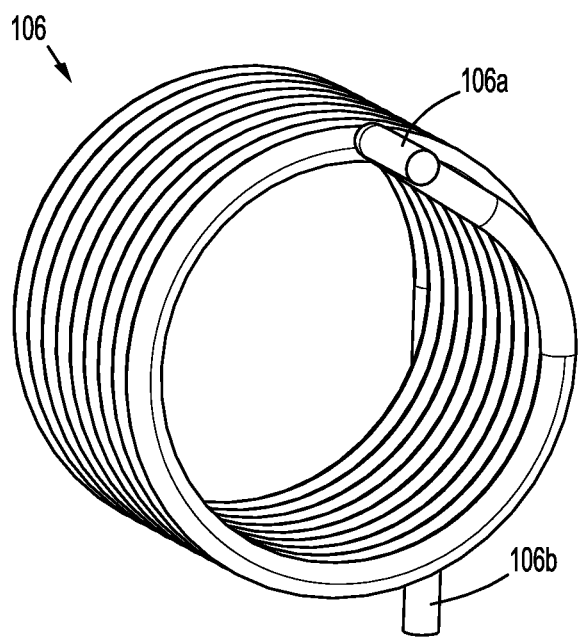
FIG. 4 is a perspective view of the torsion spring of the torsional insertion mechanism of FIG. 1, in accordance with aspects of the disclosure.
Figure 5:
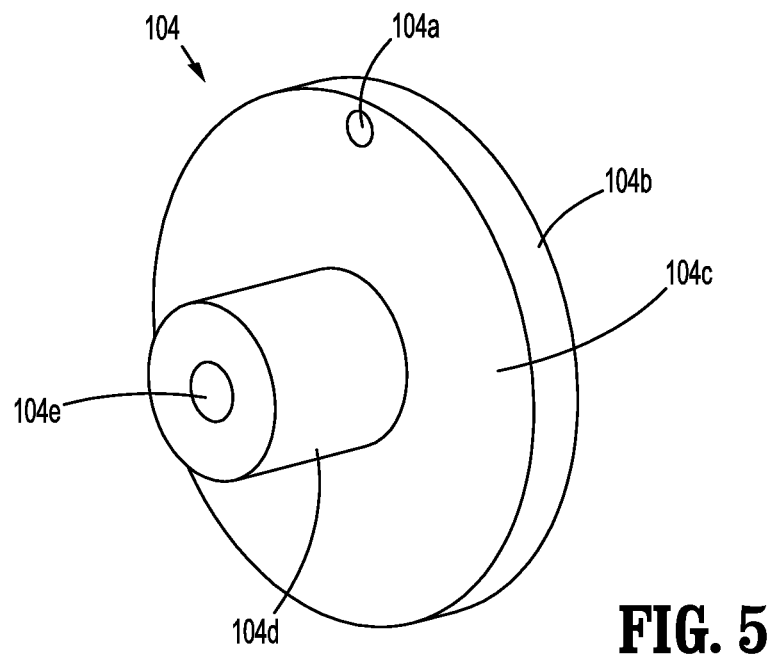
FIG. 5 is a perspective view of a crank of the torsional insertion mechanism of FIG. 1, in accordance with aspects of the disclosure.

With reference to FIG. 4, torsion spring 106 of the torsional insertion mechanism 100 is shown. The torsion spring 106 is configured to store potential energy and, when fired, convert the potential energy into kinetic energy that causes rotational motion of the crank 104. The torsion spring 106 may be fired using any of a variety of trigger mechanisms (e.g., trigger mechanism 902 of FIG. 9) that selectively enable rotation of the crank 104. The torsion spring 106 is slidably disposed around the boss 110c of the housing 110. The torsion spring 106 is configured to rotate the crank 104 based on a difference between a first spring state (e.g., an unfired state) and a second spring state (e.g., a fired state). For example, the difference may be an amount of potential energy that is stored by winding the torsion spring 106 (e.g., 360 degrees). The torsion spring 106 includes a proximal portion 106a and a distal portion 106b. The proximal portion 106a of the torsion spring 106 may be retained in a throughbore 104a penetrating surface 104c of the crank 104 (FIG. 5). The torsion spring 106 may be pre-loaded (e.g., placed under tension) prior to installation in an infusion pump system (e.g., 1700 of FIG. 17) such that the torsion spring 106 stores potential energy for later use.

Referring to FIG. 5, the crank 104 is shown. Rotational motion of the crank 104 is converted into linear motion of the insertion assembly 130. The crank 104 includes a boss 104d projecting from the surface 104c and a throughbore 104a configured for retaining a proximal portion 106a of the torsion spring 106. The boss 104d includes a central opening 104e (e.g., a throughbore) that may be configured for use with an axle (not shown).

As the crank 104 rotates in response to the torsion spring 106 rotating, the insertion assembly 130 is moved in a vertical direction (e.g., in the direction of arrow A of FIG. 2, in an insertion direction toward the skin of the patient). This is achieved based on the proximal portion 106a of the torsion spring 106 moving within a horizontal slot 122c of the trocar slider 122 (FIG. 6) and along a carrier slot 120b of the conduit carrier 120 (FIG. 7B), thereby causing the insertion assembly 130 to move in a downward direction from a first position (FIG. 1) to a second position corresponding to emergence of the piercing portion 122a of the trocar slider 122 and a distal portion 125b of the tubing 125 from the bottom of the housing 110. As the crank 104 continues to rotate, the trocar slider 122 (but not the conduit carrier 120) is moved in an upward direction back to the first position, thereby retracting the trocar slider 122 (but not the conduit carrier 120) back into the housing 110. Thus, the distal portion 125b of the tubing 125 may remain in a patient for fluid delivery (e.g., of a medicament such as insulin).

Figure 6:
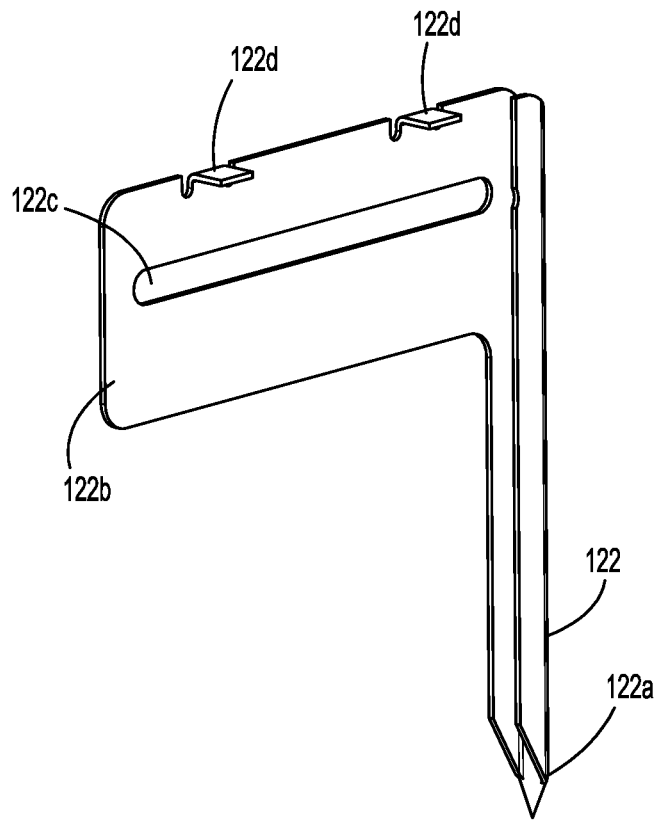
FIG. 6 is a perspective view of a trocar slider of the torsional insertion mechanism of FIG. 1, in accordance with aspects of the disclosure.
Figure 7A:
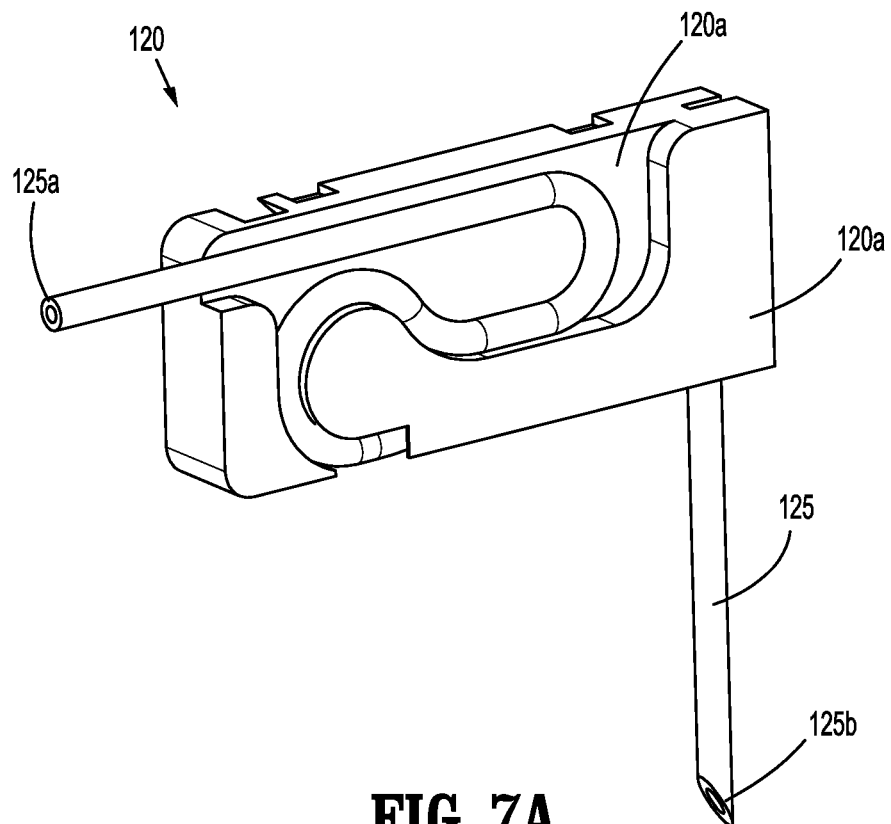
FIGS. 7A and 7B are perspective views of a conduit carrier of the torsional insertion mechanism of FIG. 1, in accordance with aspects of the disclosure.
Figure 7B:
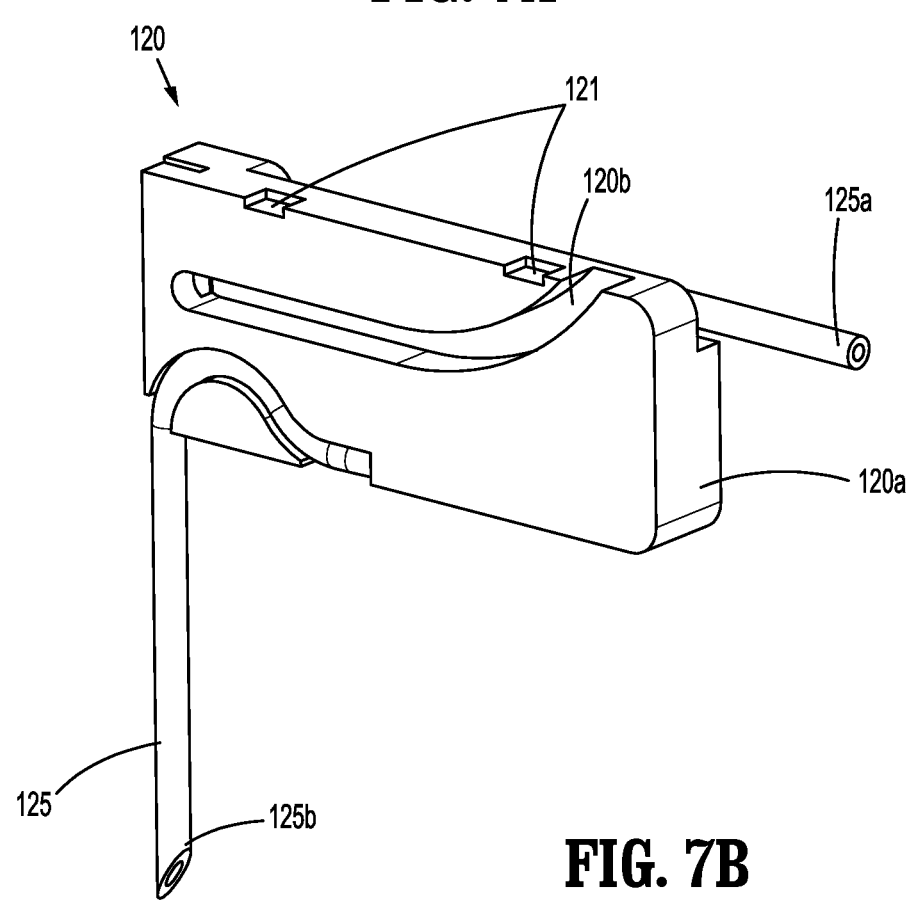

Referring to FIGS. 6, 7A, and 7B, components of the insertion assembly 130 of the torsional insertion mechanism 100 of FIG. 1 are shown. The insertion assembly 130 is configured to pierce tissue using a piercing portion 122a of a trocar slider 122 (FIG. 6) and/or a bevel of a distal portion 125b of tubing 125 (FIG. 2), thereby inserting the distal portion 125b into subcutaneous tissue. In aspects, the proximal portion 125a of the tubing 125 is connected to a medicament reservoir (e.g., 1704 of FIG. 17). This feature has the benefit of a single fluid conduit that connects the medicament reservoir to subcutaneous tissue. The insertion assembly 130 generally includes a trocar slider 122 and a conduit carrier 120. The conduit carrier 120 may be slidably disposed along the trocar slider 122. The insertion assembly 130 is configured to move between a first position and a second position in response to rotation of the crank 104. The first position of insertion assembly 130 may be a proximal position, and the second position of insertion assembly 130 may be a distal position. Components of the insertion assembly 130 are configured to move up and/or down or translate axially relative to a longitudinal axis defined by the distal portion 125b of the tubing 125. In operation, during insertion of the distal portion 125b through skin and into subcutaneous tissue, the trocar slider 122 may move downward (e.g., in a direction toward the skin of the patient) and may push down or otherwise cause downward movement of the conduit carrier 120. In operation, the trocar slider 122 (but not the conduit carrier 120) may also move upward (e.g., in a direction away from the skin of the user) to retract the trocar slider 122. For example, the trocar slider 122 may return to the first position (FIG. 2).

Referring to FIG. 6, a perspective view of the trocar slider 122 of the insertion assembly 130 is shown. The trocar slider 122 includes an arm 122b, a slot 122c through the arm 122b, one or more tabs 122d configured for moving the conduit carrier 120 from the first position to the second position, and a piercing portion 122a. The piercing portion 122a is configured to emerge from the bottom of the housing 110 to pierce the skin of a user and facilitate placement of the distal end 125b of the tubing 125 in subcutaneous tissue of the user. The slot 122c is configured to interact with the proximal portion of the torsion spring 106. The slot 122c is configured to convert the rotational motion of the crank 104 into linear motion. In aspects, the trocar slider 122 may have a "U"-shaped cross-section for accommodating at least part of the tubing 125 (e.g., the distal portion 125b).

Referring to FIGS. 7A and 7B, the conduit carrier 120 of the insertion assembly 130 of FIG. 1 is shown. The conduit carrier 120 is configured to move in response to the motion of the trocar slider 122. The conduit carrier 120 of insertion assembly 130 generally includes the tubing 125 configured for fluid communication with a medicament reservoir (e.g., 1704 of FIG. 17), which is configured for holding a fluid medicament (e.g., insulin). A fluid flow path may pass from the medicament reservoir through the tubing 125 in the conduit carrier 120. The conduit carrier 120 may include a carrier slot 120b configured to convert the rotational motion of the crank 104 into linear motion. The carrier slot 120b may include a curved portion comprising an open end configured for allowing the proximal portion 106a of the torsion spring 106 to disengage the conduit carrier 120. Thus, rotational motion of the crank 104 may cause the conduit carrier 120 to move from the first position to the second position, where the conduit carrier 120 may remain.

Figure 8C:
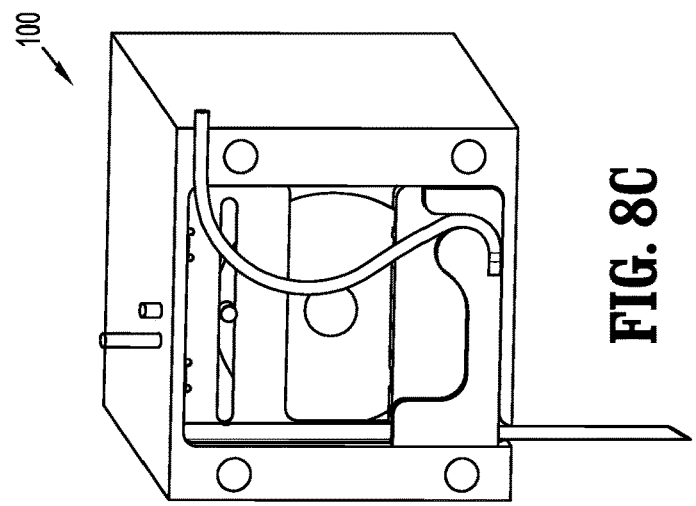
FIGS. 8A-8C are progressive side views of the insertion assembly 130 of the torsional insertion mechanism of FIG. 1 corresponding to the torsion spring transitioning from an unfired state to a fired state.
Figure 8B:
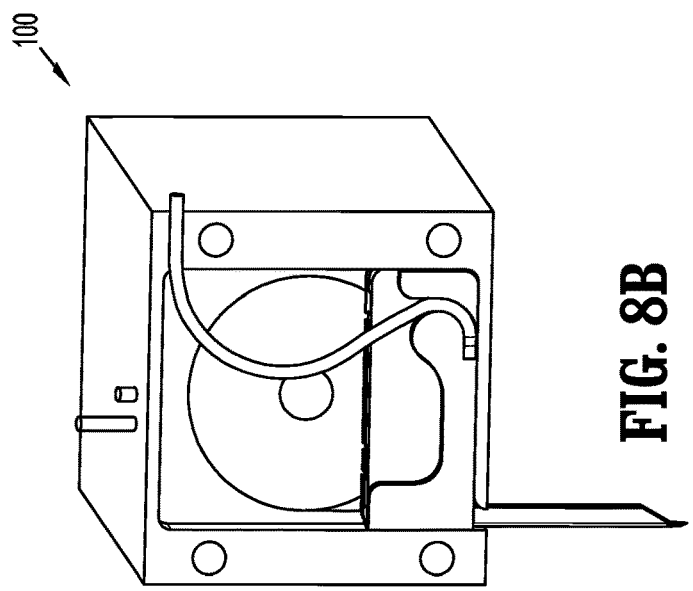
Figure 8A:
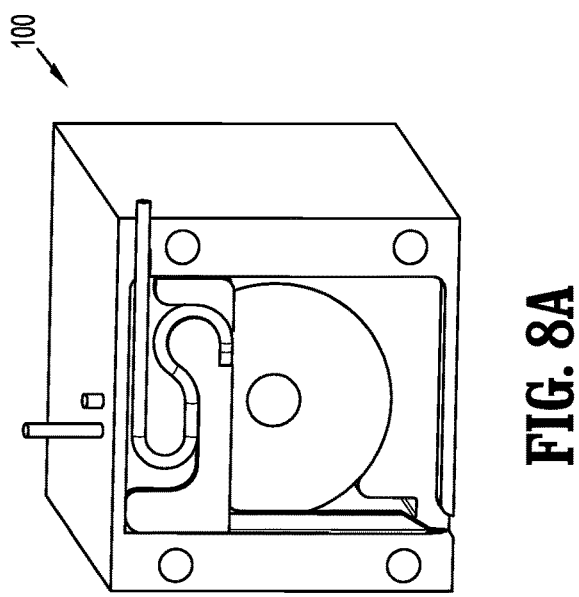

FIGS. 8A-8C are progressive views of the insertion assembly 130 of the torsional insertion mechanism 100. The insertion assembly 130 moves from the first position (FIG. 8A) to the second position (FIG. 8B), where the distal end 125b and the piercing end 122a both extend through the bottom of the housing 110. FIG. 8C shows the trocar slider 122 retracted to the first position whereas the conduit carrier 120 remains at the second position.

Figure 9:
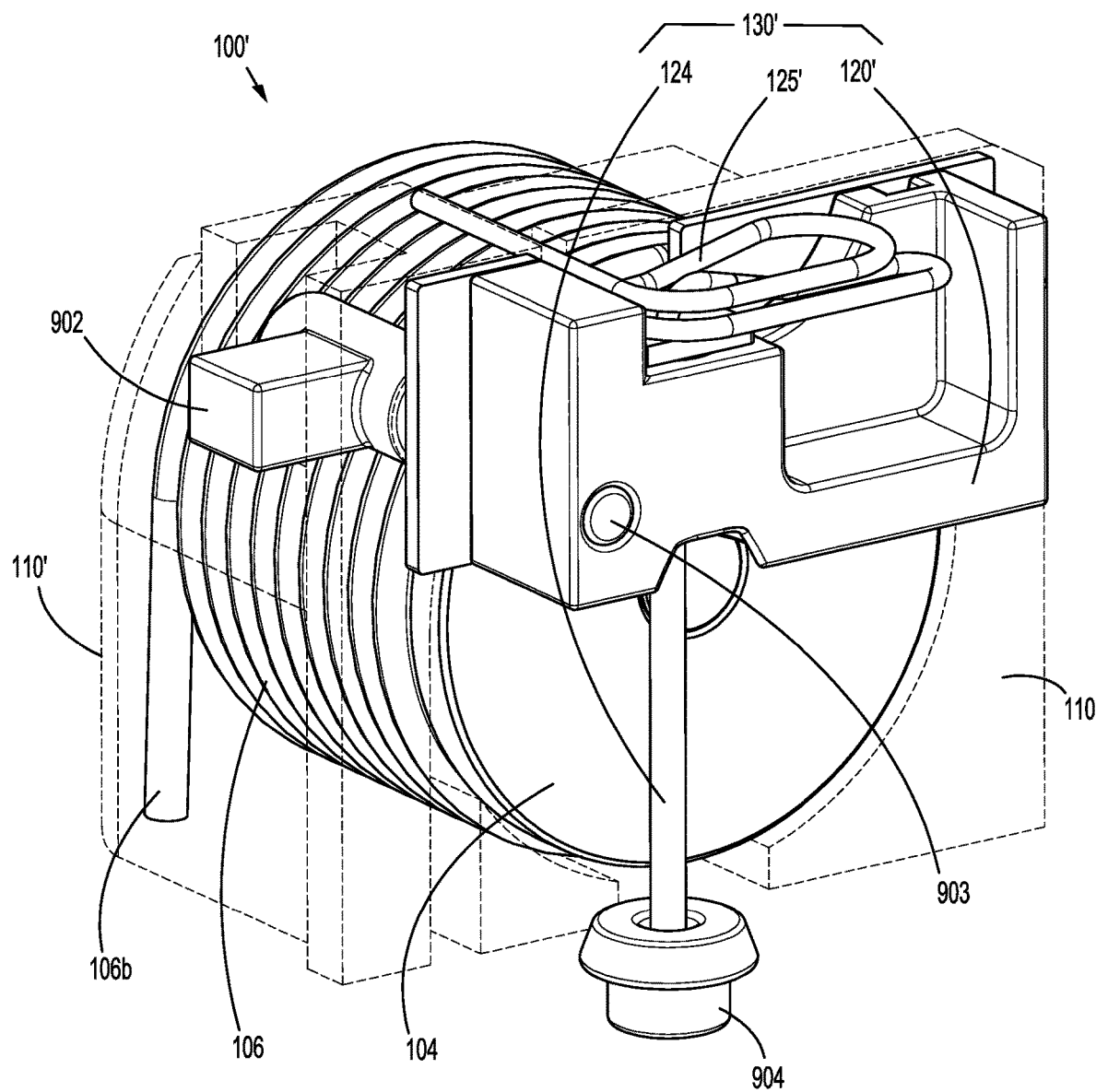
FIG. 9 is an illustration of another exemplary torsional insertion mechanism having a torsion spring, in accordance with aspects of the disclosure.
Figure 17:
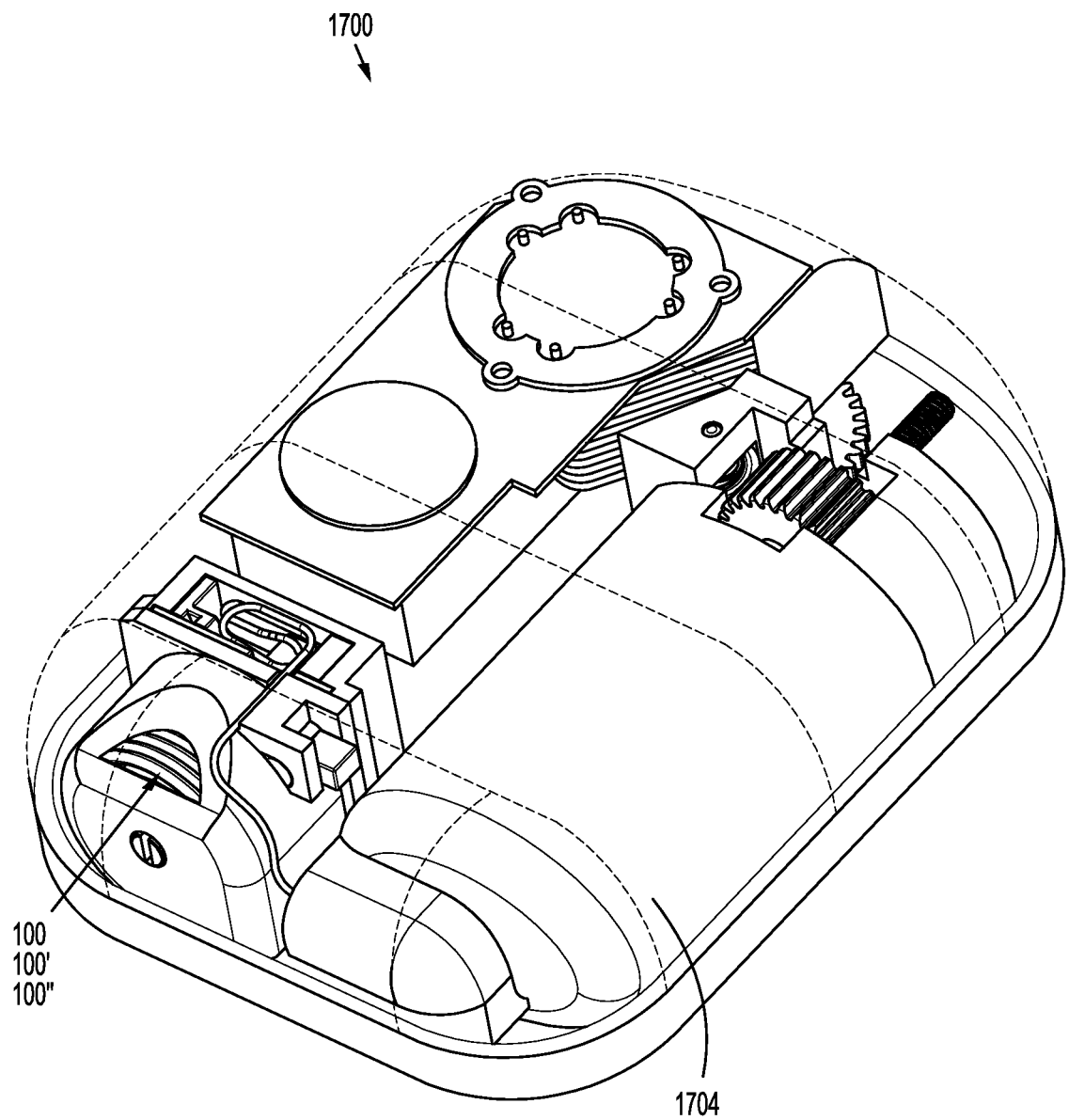
FIG. 17 is a perspective view of an exemplary infusion pump system, in accordance with aspects of the disclosure.

FIG. 9 shows another exemplary torsional insertion mechanism 100' suitable for use in an infusion pump system (e.g., 1700 of FIG. 17). Torsional insertion mechanism 100' may include a trigger mechanism 902 configured for firing the torsion spring 106. Although torsional insertion mechanism 100' shares many similarities with the torsional insertion mechanism 100 of FIG. 1, there are some differences which will be described below. Among the differences is an external fluid seal 904 that may be at least partially composed of an elastomeric material (e.g., rubber) or some other suitable material for preventing external fluid from entering the torsional insertion mechanism 100'. In aspects, a fluid flow path of FIG. 9 may include tubing 125' (e.g., a flexible tube configured for fluid communication with a medicament reservoir), a trocar 123 (FIG. 10), and a cannula 124. The cannula 124 may include a channel configured for fluid delivery and for receiving the trocar 123. In aspects, the trocar 123 may be configured for slidably moving within the channel of the cannula 124.

Figure 10:
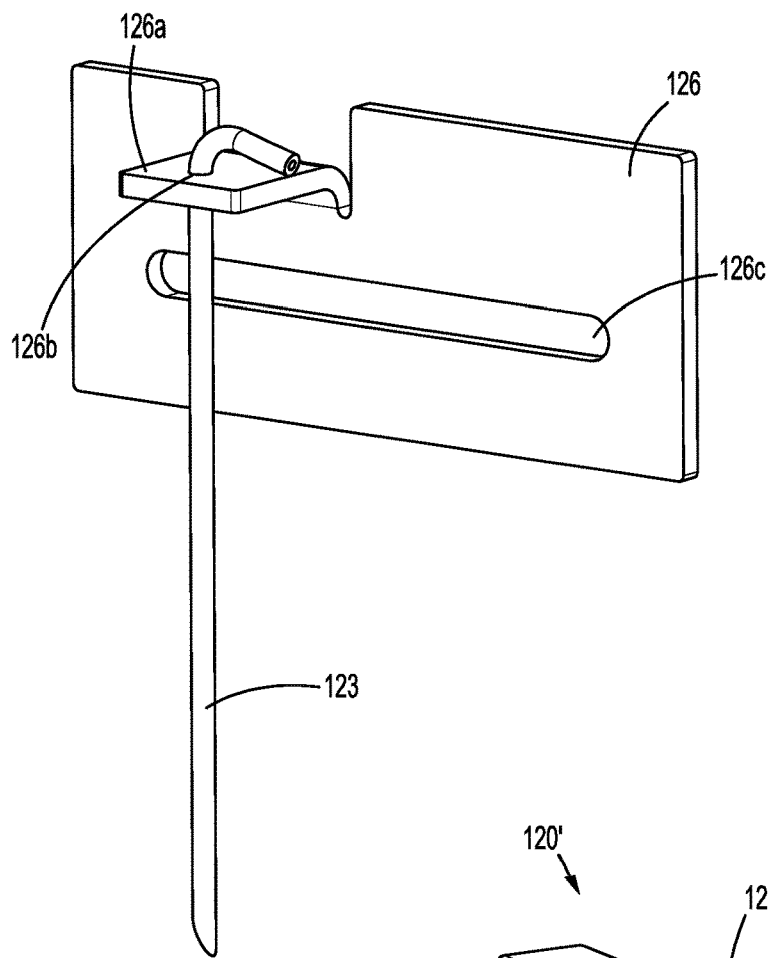
FIG. 10 is a perspective view of a trocar slider of the torsional insertion mechanism of FIG. 9, in accordance with aspects of the disclosure.

The torsional insertion mechanism 100' includes an insertion assembly 130' comprising a conduit carrier 120' and a trocar slider 126 (FIG. 10). The conduit carrier 120' is configured to move in response to the motion of the trocar slider 126, which includes a tab 126a configured for moving the conduit carrier 120' from a first position to a second position. The conduit carrier 120' includes tubing 125'. A fluid flow path may pass from a medicament reservoir (e.g., 1704 of FIG. 17) through the tubing 125' in the conduit carrier 120'. The conduit carrier 120' may include a carrier slot 120b (FIG. 12) configured to convert rotational motion of a crank 104 into linear motion. The carrier slot 120b may include a curved portion comprising an open end configured for allowing a proximal portion (not shown but similar to the proximal portion 106a of FIG. 4) of a torsion spring 106 to disengage the conduit carrier 120'. The conduit carrier 120' moves from the first position to the second position in response to the rotational motion of the crank 104.

The trigger mechanism 902 may be a latch or some other suitable mechanism used to fire the torsion spring 106 by engaging or disengaging a notch in a side surface (not shown but similar to surface 104b of FIG. 5) of the crank 104, thereby preventing or permitting rotation of the crank 104. Toggling the trigger mechanism 902 may disengage the trigger mechanism 902 from the crank 104, and the crank 104 may rotate in response to stored potential energy in the torsion spring 106 being converted to kinetic energy. The torsion spring 106 (which may be pre-loaded) may apply torque to the crank 104, thereby causing the crank 104 to rotate based on a difference between a first spring state (e.g., an unfired state) and a second spring state (e.g., a fired state).

In aspects, the conduit carrier 120' of the torsional insertion mechanism 100' may include a magnet 903. The magnet 903 may be used to sense the relative location and/or the fired status of the conduit carrier 120'. For example, the magnet 903 may interact with a sensor (e.g., a Hall effect sensor) configured to output an electrical signal based on a detected proximity of the magnet 903.

Figure 11:
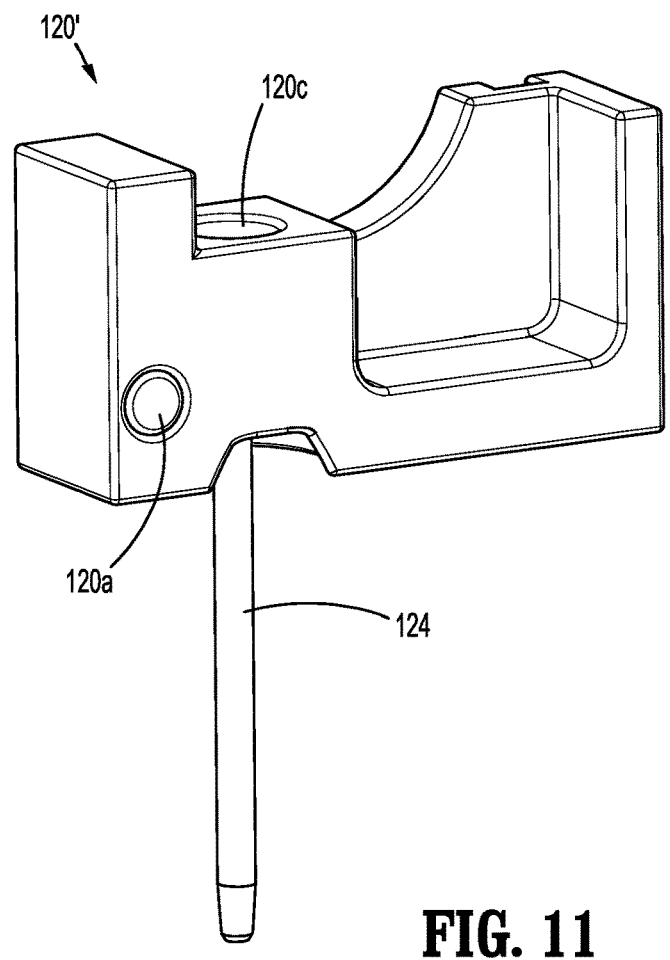
FIGS. 11 and 12 are perspective views of a conduit carrier of the torsional insertion mechanism of FIG. 9, in accordance with aspects of the disclosure.
Figure 12:
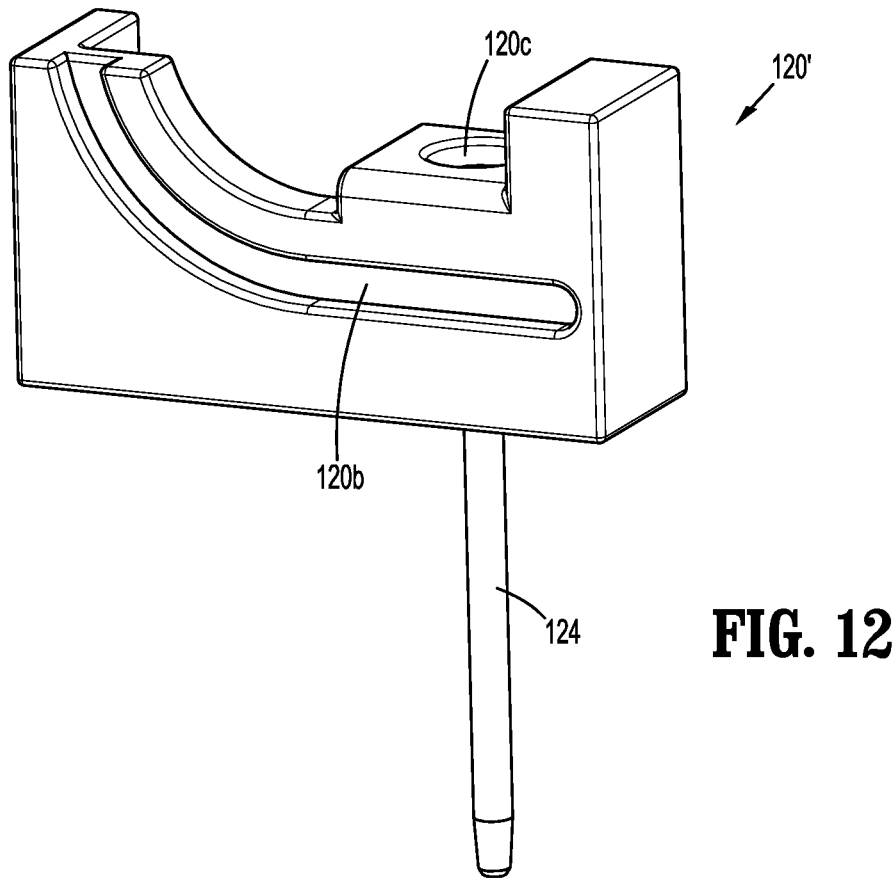
Figure 13:
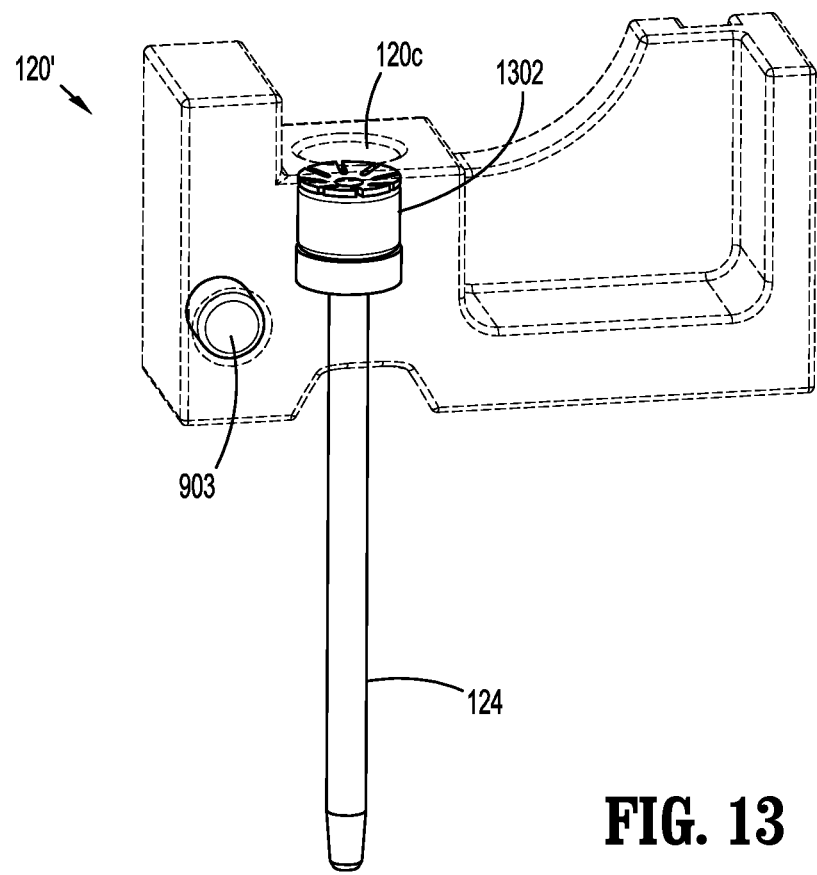
FIG. 13 is a cutaway perspective view of the conduit carrier of FIG. 11, in accordance with aspects of the disclosure.

The torsional insertion mechanism 100' may include a trocar slider 126 (FIG. 10) that may include a trocar 123 configured to support a cannula 124 (e.g., a soft flexible tube or the like) and enable skin penetration. For example, the trocar 123 may be configured to slide within the cannula 124 and extend out of the distal end of the cannula 124, thereby providing rigidity and/or serving as a guide when the bevel of the trocar 123 pierces skin. The torsional insertion mechanism 100' may include a conduit carrier 120' (FIGS. 11-13) that includes the magnet 903, a trocar seal 1302 (FIG. 13), and a trocar seal retainer 120c (FIGS. 11-13). The trocar seal 1302 may be at least partially composed of an elastomeric material (e.g., rubber) or some other suitable material for providing a fluid-tight seal between the trocar 123 and the cannula 124. The trocar seal retainer 120c may be an opening in the housing of the conduit carrier 120', and the opening may be configured to accommodate the trocar seal 1302 and/or to secure the trocar seal 1302 to the conduit carrier 120' (e.g., via a frictional fit).

Figure 14:
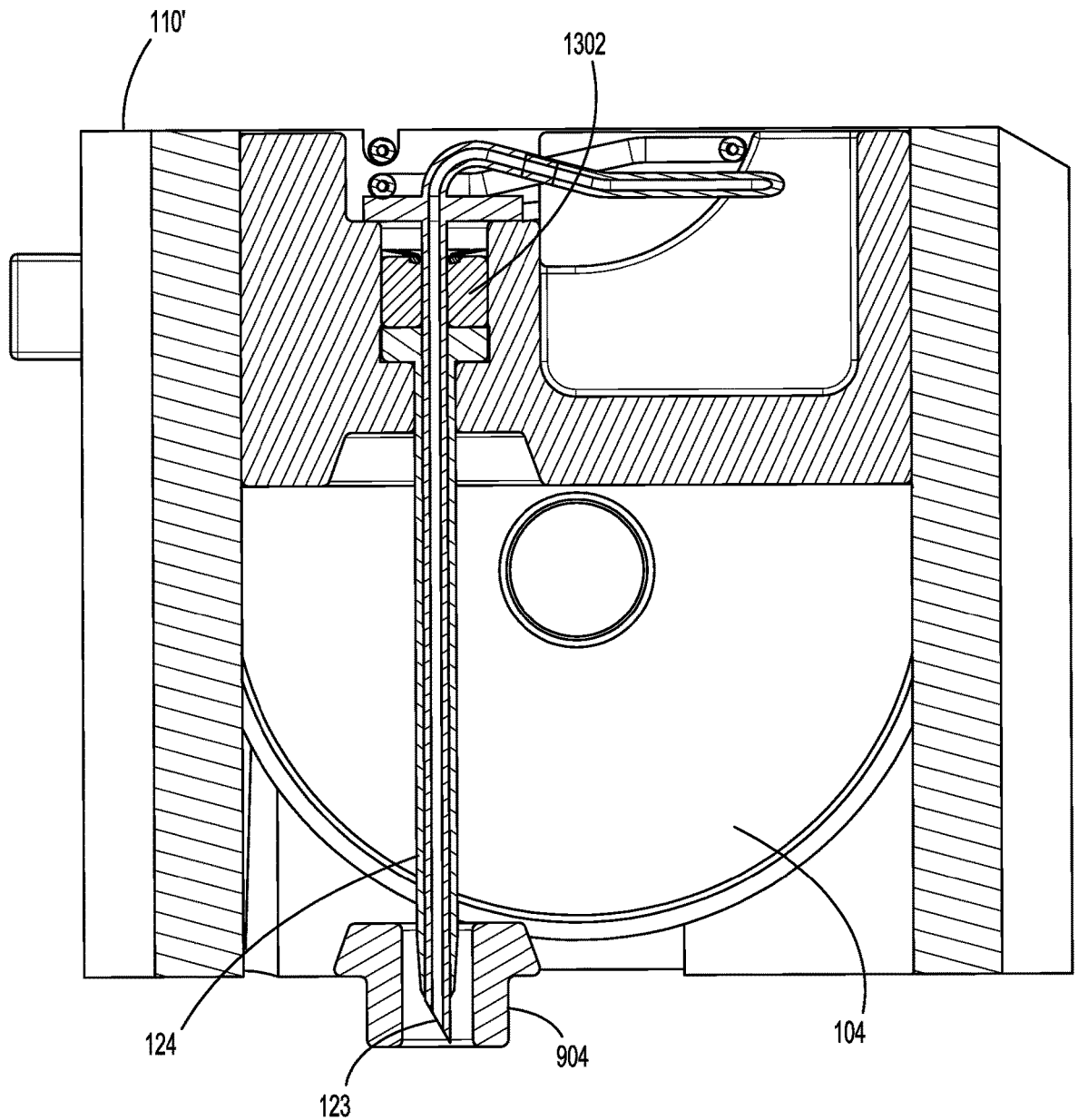
FIG. 14 is a cutaway side view of the torsional insertion mechanism of FIG. 9, in accordance with aspects of the disclosure.

FIG. 14 shows a side cutaway view of the torsional insertion mechanism 100' of FIG. 9. Among other elements, FIG. 14 shows the conduit carrier 120' and depicts the trocar 123 within the cannula 124. In the example of FIG. 14, firing the torsional insertion mechanism 100' causes the conduit carrier 120' to move downward such that both the trocar 123 and the cannula 124 emerge from the external fluid seal 904 for insertion into a patient. However, the trocar 123 may move independently from the cannula 124 such that the distal end of the trocar 123 can be pulled up and away from the distal end of the inserted cannula 124 but not far enough to be outside of the trocar seal 1302 (e.g., such that the distal end of the trocar 123 is moved to a position within the cannula 124 but closer to the proximal end of the cannula 124). The external fluid seal 904 may engage (e.g., push against for a frictional fit) the conduit carrier 120' upon insertion, thereby preventing external fluid from entering the torsional insertion mechanism 100'.

Figure 15:
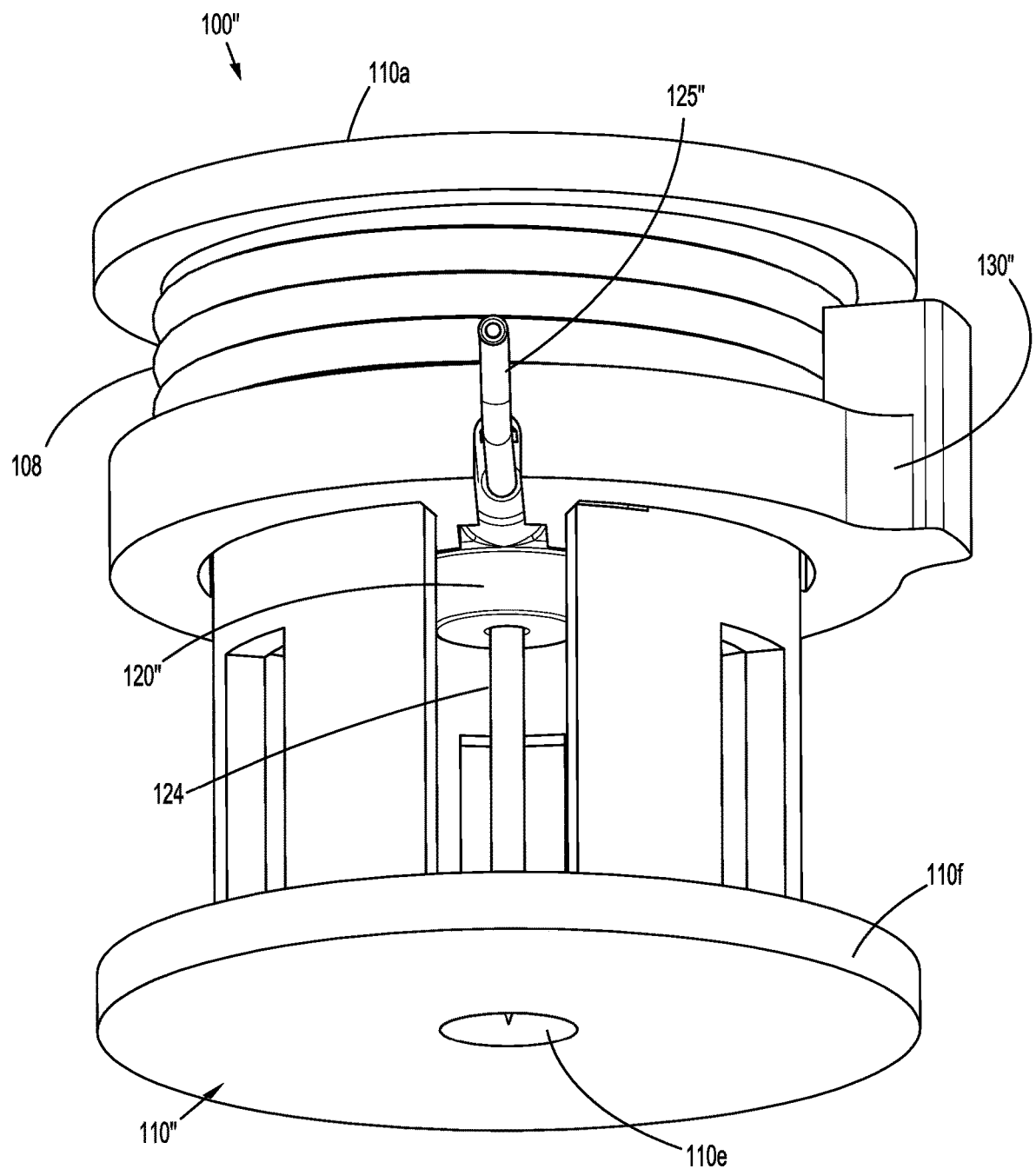
FIG. 15 is a side perspective view of a tube connected insertion mechanism, in accordance with aspects of the disclosure.
Figure 16:
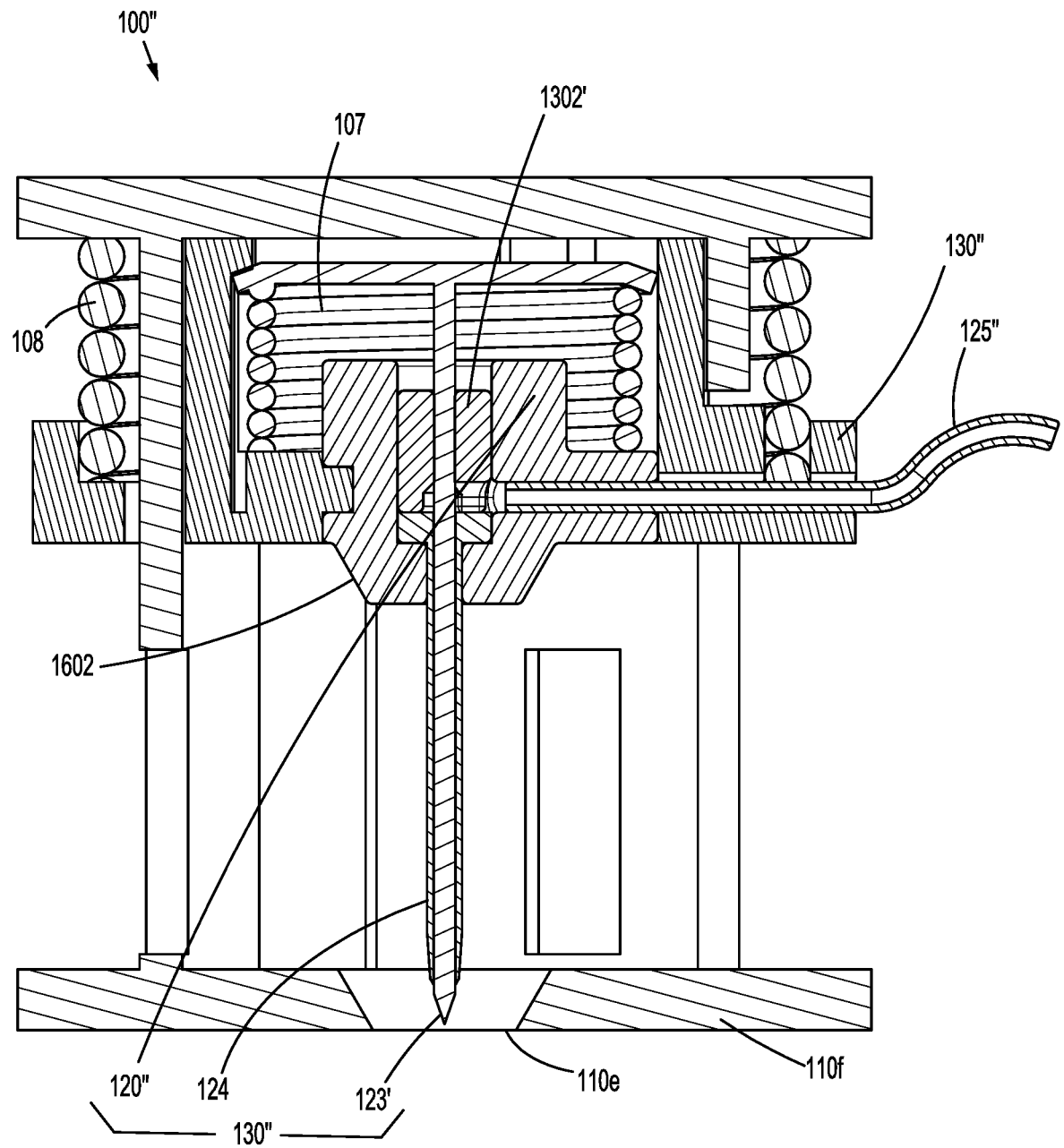
FIG. 16 is a cutaway side view of the tube connected insertion mechanism of FIG. 15, in accordance with aspects of the disclosure.

FIG. 15 shows an exemplary insertion mechanism 100" with a first compression spring 108 and a second compression spring 107 (FIG. 16) suitable for use in an infusion pump system (e.g., 1700 of FIG. 17). FIG. 16 shows a side cross-section view of the insertion mechanism 100" in an unfired state (e.g., a first state). The insertion mechanism 100" includes an insertion assembly 130" comprising a trocar 123' (or, for example, a captive introducer needle) and a conduit carrier 120". The trocar 123' is configured to pierce tissue and facilitate insertion of a cannula 124 into subcutaneous tissue for fluid delivery. The conduit carrier 120" has a first opening through which the cannula 124 extends, a second opening through which tubing 125" (e.g., a flexible tube connected to a fluid reservoir) extends, and a third opening in which a trocar seal 1302' is disposed (e.g., via frictional engagement). A benefit of this design is that it provides a pre-assembled fluid pathway between a fluid reservoir (e.g., 1704 of FIG. 17) and the cannula 124 while retaining a shape factor similar to existing inserter designs (e.g., the inserter design described in U.S. patent application Ser. No. 16/038,049 titled AMBULATORY INFUSION PUMPS AND ASSEMBLIES FOR USE WITH SAME and filed Jul. 17, 2018, the entirety of which is incorporated by reference herein).

The insertion mechanism 100" also includes a housing 110" comprising a first portion 110a and a second portion 110f. The insertion assembly 130" is slidably disposed between the first portion 110a and the second portion 110f, but movement of the insertion assembly 130" may be controlled by a trigger mechanism (e.g., a latch configured to engage and disengage a notch in the insertion assembly 130"). The insertion assembly 130" is configured to cooperate with the first portion 110a to retain the spring 108. In aspects, the insertion assembly 130" may be integrated with the conduit carrier 120" such that movement of the insertion assembly 130" is accompanied by corresponding movement of the conduit carrier 120". Thus, when the spring 108 is fired (e.g., allowed to transition from a compressed state to an uncompressed state by a trigger mechanism), the insertion assembly 130" moves linearly (e.g., downward) relative to the first portion 110a, thereby causing to the conduit carrier 120" to move similarly in response to the force exerted by the spring 108.

The conduit carrier 120″ may be at least partially composed of an elastomeric material (e.g., rubber) or some other suitable material for forming a fluid-tight seal between a portion 1602 (e.g., a bottom portion) of the conduit carrier 120″ and an opening 110e in the housing 110″. When the spring 108 is fired, it may exert a downward force on the insertion assembly 130″, thereby causing the conduit carrier 120″ to move downward from a first position depicted in FIG. 16 to a second position at which the portion 1602 mates with the opening 110e to prevent fluid ingress. At the second position, the cannula 124 and the trocar 123′ extend through the opening 110e in the housing 110″.

Movement of the conduit carrier 120″ to the second position permits the second compression spring 107 to fire (e.g., transition from a compressed state to an uncompressed state), thereby allowing the trocar 123′ to return to the first position (e.g., by exerting an upward force on the trocar 122′ that pulls the trocar 123′ out of the cannula 124 and out of the way of the fluid flow path). As depicted in FIG. 16, the trocar 123′ may be a solid needle that is coupled to (e.g., integrated with) the second compression spring 107. When the trocar 123′ returns to the first position, the distal end of the trocar 123′ may be located within the trocar seal 1302′ in such a manner that avoids obstructing the fluid flow path while preventing fluid from escaping through the third opening. In aspects, tubing 125″ may be a portion of the fluid flow path that moves with the conduit carrier 120″.

FIG. 17 shows an exemplary infusion pump system 1700, in accordance with aspects of the disclosure. The infusion pump system 1700 may be a wearable patch pump that includes a fluid conduit insertion mechanism 100, 100′, or 100″ (FIGS. 1, 9, and 15), and a medicament reservoir 1704 in fluid communication with the fluid conduit insertion mechanism 100, 100′, or 100″.

The phrases "in an embodiment," "in embodiments," "in various embodiments," "in some embodiments," or "in other embodiments" may each refer to one or more of the same or different embodiments in accordance with the disclosure. A phrase in the form "A or B" means "(A), (B), or (A and B)." A phrase in the form "at least one of A, B, or C" means "(A); (B); (C); (A and B); (A and C); (B and C); or (A, B, and C)." It should be understood that the foregoing description is only illustrative of the disclosure. To the extent consistent, any or all of the aspects detailed herein may be used in conjunction with any or all of the other aspects detailed herein. Various alternatives and modifications can be devised by those skilled in the art without departing from the disclosure. Accordingly, the disclosure is intended to embrace all such alternatives, modifications, and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

Some example embodiments are provided below.

Example 1. A torsional insertion mechanism, comprising:
a torsion spring configured to rotate a crank based on a difference between a first spring state and a second spring state; and
an insertion assembly coupled to the crank and configured to move from a first position to a second position in response to rotation of the crank, the insertion assembly including a cannula carrier and a trocar slider configured to pierce tissue, wherein the trocar slider is slidably disposed along the cannula carrier and configured to separate from the cannula carrier upon piercing tissue.

Example 2. The torsional insertion mechanism according to example 1, wherein the cannula carrier includes a cannula configured for insertion into tissue in response to rotational motion of the crank.

Example 3. The torsional insertion mechanism according to example 1, wherein the trocar slider includes a trocar slidably disposed inside of the cannula, and wherein the trocar is configured to pierce tissue in response to rotational motion of the crank.

Example 4. The torsional insertion mechanism according to example 1, wherein the trocar slider includes a tab configured for moving the cannula carrier into the second position.

Example 5. The torsional insertion mechanism according to example 1, further comprising a housing configured to retain a distal portion of the torsion spring, and wherein the torsion spring includes a proximal portion configured to engage with the crank and a slot of the trocar slider.

Example 6. The torsional insertion mechanism according to example 1, further comprising a trigger mechanism configured to selectively enable rotation of the crank.

Example 7. The torsional insertion mechanism according to example 6, wherein the trigger mechanism is configured to engage a recess in the crank to prevent rotation of the crank and to disengage the recess in the crank to enable rotation of the crank.

Example 8. The torsional insertion mechanism according to example 2, wherein the insertion assembly further includes:
a fluid flow path that passes through the cannula in the cannula carrier, wherein the fluid flow path is configured for fluid communication between the cannula and a medicament reservoir.

Example 9. The torsional insertion mechanism according to example 1, wherein the trocar slider and the cannula carrier are configured to move together from the first position to the second position.

Example 10. The torsional insertion mechanism according to example 1, wherein the trocar slider is configured to return to the first position while the cannula carrier remains in the second position.

Example 11. An infusion pump system, comprising:
a torsional insertion mechanism, including:
a torsion spring configured to rotate a crank based on a difference between a first spring state and a second spring state; and
an insertion assembly coupled to the crank and configured to move from a first position to a second position in response to rotation of the crank, the insertion assembly including a cannula carrier and a trocar slider configured to pierce tissue, wherein the trocar slider is slidably disposed along the cannula carrier and configured to separate from the cannula carrier upon piercing tissue.

Example 12. The infusion pump system according to example 11, wherein the cannula carrier includes a cannula configured for insertion into tissue in response to rotational motion of the crank.

Example 13. The infusion pump system according to example 11, wherein the trocar slider includes a trocar slidably disposed inside of the cannula, and wherein the trocar is configured to pierce tissue in response to rotational motion of the crank.

Example 14. The infusion pump system according to example 11, wherein the trocar slider includes a tab configured for moving the cannula carrier into the second position.

Example 15. The infusion pump system according to example 11, wherein the torsional insertion mechanism further includes a housing configured to retain a distal portion of the torsion spring, and wherein the torsion spring includes a proximal portion configured to engage with the crank and a slot of the trocar slider.

Example 16. The infusion pump system according to example 11, wherein the torsional insertion mechanism further includes a trigger mechanism configured to selectively enable rotation of the crank.

Example 17. The infusion pump system according to example 11, wherein the trocar slider and the cannula carrier are configured to move together from the first position to the second position, and wherein the trocar slider is configured to return to the first position while the cannula carrier remains in the second position.

Example 18. A method for operating a torsional insertion mechanism of an insulin infusion system, the method comprising:
  rotating a crank based on a difference between a first spring state and a second spring state of a torsion spring;
  moving a trocar slider and a cannula carrier from a first position to a second position in response to rotation of the crank; and
  returning the trocar slider to the first position while leaving the cannula carrier in the second position in response to continued rotation of the crank.

Example 19. The method according to example 18, wherein moving the trocar slider and the cannula carrier from the first position to the second trocar position includes piercing tissue with the trocar slider.

Example 20. The method according to example 18, wherein returning the trocar slider to the first position while leaving the cannula carrier in the second position includes disengaging the crank from the cannula carrier via an open-ended slot of the cannula carrier.

Example 21. An insertion mechanism, comprising:
  a first compression spring configured to exert a linear force based on a difference between a compressed state and an uncompressed state; and
  an insertion assembly configured to move from a first position to a second position in response to the linear force exerted by the first compression spring, the insertion assembly including a conduit carrier and a trocar configured to pierce tissue, the conduit carrier including a first opening through which extends a cannula and a second opening through which extends tubing connected to a fluid reservoir, the trocar being slidably disposed within the cannula.

Example 22. The insertion mechanism according to example 21, wherein the conduit carrier and the trocar are configured to move together from the first position to the second position.

Example 23. The insertion mechanism according to example 21, wherein the trocar is configured to return to the first position while the conduit carrier remains in the second position.

Example 24. The insertion mechanism according to example 21, further comprising a second compression spring configured to return the trocar to the first position.

Example 25. The insertion mechanism according to example 21, further comprising a second compression spring coupled to the trocar.

Example 26. The insertion mechanism according to example 21, wherein the trocar is a solid needle integrated with a second compression spring configured to return the trocar to the first position.

Example 27. The insertion mechanism according to example 21, further comprising a second compression spring configured to move the trocar outside of the cannula.

Example 28. The insertion mechanism according to example 21, wherein the conduit carrier further includes a third opening in which a trocar seal is disposed.

Example 29. The insertion mechanism according to example 28, wherein the trocar is slidably disposed within the trocar seal.

Example 30. The insertion mechanism according to example 28, wherein a distal end of the trocar moves to a location within the trocar seal when the trocar returns to the first position while the conduit carrier remains in the second position.

Example 31. An infusion pump system, comprising:
  an insertion mechanism, including:
    a first compression spring configured to exert a linear force based on a difference between a compressed state and an uncompressed state; and
    an insertion assembly configured to move from a first position to a second position in response to the linear force exerted by the first compression spring, the insertion assembly including a conduit carrier and a trocar configured to pierce tissue, the conduit carrier including a first opening through which extends a cannula and a second opening through which extends tubing connected to a fluid reservoir, the trocar being slidably disposed within the cannula.

Example 32. The infusion pump system according to example 31, wherein the trocar is configured to return to the first position while the conduit carrier remains in the second position.

Example 33. The infusion pump system according to example 31, further comprising a second compression spring configured to return the trocar to the first position.

Example 34. The infusion pump system according to example 31, wherein the trocar is a solid needle integrated with a second compression spring configured to return the trocar to the first position.

Example 35. The infusion pump system according to example 31, further comprising a second compression spring configured to move the trocar outside the cannula.

Example 36. The infusion pump system according to example 31, wherein the conduit carrier further includes a third opening in which a trocar seal is disposed.

Example 37. The infusion pump system according to example 36, wherein a distal end of the trocar moves to a location within the trocar seal when the trocar returns to the first position while the conduit carrier remains in the second position.

Example 38. A method for operating an insertion mechanism of an insulin infusion system, the method comprising:
  moving a trocar and a conduit carrier from a first position to a second position in response to a force exerted by a first compression spring, the conduit carrier including a first opening through which extends a cannula and a second opening through which extends tubing connected to a fluid reservoir, the trocar blocking a connection between the cannula and the tubing; and
  returning the trocar to the first position while leaving the conduit carrier in the second position in response to a force exerted by a second compression spring, thereby permitting the connection between the cannula and the tubing.

Example 39. The method according to example 38, wherein moving the trocar from the first position to the second position causes the trocar to pierce tissue and insert the cannula in the tissue.

Example 40. The method according to example 39, wherein the conduit carrier further includes a third opening in which a trocar seal is disposed, and wherein returning the trocar to the first position includes moving a distal end of the trocar to a location within the trocar seal.

What is claimed is:

1. A torsional insertion mechanism, comprising:
    a torsion spring configured to rotate a crank based on a difference between a first spring state and a second spring state; and
    an insertion assembly including a conduit carrier and a trocar slider that is slidably disposed along the conduit carrier and configured to pierce tissue, wherein the conduit carrier comprises a first slot and the trocar slider comprises a second slot, wherein the crank is coupled to the conduit carrier and the trocar slider via the first and second slots such that the insertion assembly is configured to move from a first position to a second position in response to rotation of the crank,
    wherein the crank is configured to decouple from the conduit carrier such that the trocar slider separates from the conduit carrier after piercing tissue.

2. The torsional insertion mechanism according to claim 1, wherein the conduit carrier includes a flexible tube having a distal portion configured for insertion into tissue in response to rotational motion of the crank.

3. The torsional insertion mechanism according to claim 2, wherein the insertion assembly further includes:
    a fluid flow path that passes through the flexible tube in the conduit carrier, wherein the fluid flow path is configured for fluid communication between the distal portion of the flexible tube and a medicament reservoir.

4. The torsional insertion mechanism according to claim 1, wherein the trocar slider is configured to pierce tissue in response to rotational motion of the crank.

5. The torsional insertion mechanism according to claim 1, wherein the trocar slider includes a tab configured for moving the conduit carrier into the second position.

6. The torsional insertion mechanism according to claim 1, further comprising a housing configured to retain a distal portion of the torsion spring, and wherein the torsion spring includes a proximal portion configured to engage with the crank and the second slot of the trocar slider.

7. The torsional insertion mechanism according to claim 1, further comprising a trigger mechanism configured to selectively enable rotation of the crank.

8. The torsional insertion mechanism according to claim 1, wherein the trocar slider and the conduit carrier are configured to move together from the first position to the second position.

9. The torsional insertion mechanism according to claim 1, wherein the trocar slider is configured to return to the first position from the second position while the conduit carrier remains in the second position.

10. An infusion pump system, comprising:
    a torsional insertion mechanism, including:
        a torsion spring configured to rotate a crank based on a difference between a first spring state and a second spring state; and
        an insertion assembly including a conduit carrier and a trocar slider that is slidably disposed along the conduit carrier and configured to pierce tissue, wherein the conduit carrier comprises a first slot and the trocar slider comprises a second slot, wherein the crank is coupled to the conduit carrier and the trocar slider via the first and second slots such that the insertion assembly is configured to move from a first position to a second position in response to rotation of the crank, wherein the crank is configured to decouple from the conduit carrier such that the trocar slider separates from the conduit carrier after piercing tissue.

11. The infusion pump system according to claim 10, wherein the conduit carrier includes a flexible tube having a distal portion configured for insertion into tissue in response to rotational motion of the crank.

12. The infusion pump system according to claim 10, wherein the trocar slider is configured to pierce tissue in response to rotational motion of the crank.

13. The infusion pump system according to claim 10, wherein the trocar slider includes a tab configured for moving the conduit carrier into the second position.

14. The infusion pump system according to claim 10, wherein the torsional insertion mechanism further includes a housing configured to retain a distal portion of the torsion spring, and wherein the torsion spring includes a proximal portion configured to engage with the crank and the second slot of the trocar slider.

15. The infusion pump system according to claim 10, wherein the torsional insertion mechanism further includes a trigger mechanism configured to selectively enable rotation of the crank.

16. The infusion pump system according to claim 10, wherein the trocar slider and the conduit carrier are configured to move together from the first position to the second position.

17. The infusion pump system according to claim 10, wherein the trocar slider is configured to return to the first position from the second position while the conduit carrier remains in the second position.

18. A method for operating a torsional insertion mechanism of an insulin infusion system, the method comprising:
    rotating a crank based on a difference between a first spring state and a second spring state of a torsion spring;
    moving a trocar slider and a conduit carrier from a first position to a second position in response to rotation of the crank, wherein the conduit carrier comprises a first slot and the trocar slider comprises a second slot, and wherein the crank is coupled to the conduit carrier and the trocar slider via the first and second slots; and
    returning the trocar slider to the first position while leaving the conduit carrier in the second position in response to continued rotation of the crank.

19. The method according to claim 18, wherein moving the trocar slider and the conduit carrier from the first position to the second position comprises piercing tissue with at least the trocar slider.

20. The method according to claim 18, wherein the first slot of the conduit carrier is open-ended, and wherein returning the trocar slider to the first position while leaving the conduit carrier in the second position comprises disengaging the crank from the conduit carrier via the first slot.

* * * * *